United States Patent [19]

Numata et al.

[11] Patent Number: 5,358,850

[45] Date of Patent: Oct. 25, 1994

[54] SANDWICH IMMUNOASSAY OF β-N-ACETYLGLUCOSAMINIDASE AND MONOCLONAL ANTIBODY USED THEREIN

[75] Inventors: Yoshito Numata, Yao; Yoko Kosugi, Sakai; Kazunori Shibata, Osaka, all of Japan

[73] Assignee: Shionogi Seiyaku Kabushiki Kaisha, Osaka, Japan

[21] Appl. No.: 77,868

[22] Filed: Jun. 18, 1993

[30] Foreign Application Priority Data

Jun. 19, 1992 [JP] Japan .................................. 4-186194

[51] Int. Cl.⁵ ................ G01N 33/536; G01N 33/543; G01N 33/573; G01N 33/577

[52] U.S. Cl. .................................... 435/7.4; 435/7.9; 435/7.92; 435/7.94; 435/971; 435/975; 435/172.2; 435/240.27; 530/388.1; 530/388.26

[58] Field of Search ...................... 435/7.4, 7.9, 7.92, 435/7.94, 172.2, 70.21, 240.27, 975, 971; 436/530; 530/388.1, 388.26

[56] References Cited

U.S. PATENT DOCUMENTS 4,486,530 12/1984 David et al. ..................... 435/7.1

OTHER PUBLICATIONS

Clinical Chemistry, vol. 29, No. 10, 1983, pp. 1713–1716, Akira Moto, et al., "Simple, Rapid Spectrophotometry of Urinary N-Acetyl-β-D-Glucosaminidase, with use of a New Chromogenic Substrate".

Clinica Chimica Acta, vol. 137, 1984, pp. 1–11, Roger Gibey, et al., "Urinary N-Acetyl-β-D-Glucosaminidase (NAG) Isoenzyme Profiles: A Tool for Evaluating Nephrotoxicity of Aminoglycosides and Cephalosporins".

Clinica Chimica Acta, vol. 130, 1983, pp. 297–304, Alessandra Vigano, et al., "N-Acetyl-β-D-Glucosaminidase (NAG) and NAG Isoenzymes in Children with Upper and Lower Urinary Tract Infections".

Clinica Chimica Acta, vol. 164, 1987, pp. 339–350, Chun-Ting Yuen, et al., "Isoenzymes of Urinary N-Acetyl-β-D-Glucosaminidase (NAG) in Patients with Renal Transplants".

Clinical Chimica Acta, vol. 64, 1975, pp. 195–202, B. G. Ellis, et al., "Presence of Serum and Tissue Forms of N-Acetyl-β-Glucosaminidase in Urine From Patients with Renal Disease".

Enzyme, vol. 28, pp. 14–17, 1982, Elja Pitkanen, et al., "Serum β-N-Acetylglucosaminidase Isoenzymes in Insulin-Dependent Diabetes Mellitus".

Clinica Chimica Acta, vol. 94, 1979, pp. 281–286, Linda V. Oberkotter, et al., "Relationship of Thyroid Status and Serum N-Acetyl-β-Glucosaminidase Isoenzyme Activities in Humans".

Scand J Clin Lab Invest, 1989, vol. 49, pp. 597–603, A. Isaksson, et al., "Enzyme Immunoassay of β-Hexosaminidase Isoenzymes Using Monoclonal Antibodies".

Primary Examiner—Esther M. Kepplinger
Assistant Examiner—Eve J. Wilson
Attorney, Agent, or Firm—Oblon, Spivak, McClelland, Maier & Neustadt

[57] ABSTRACT

The present invention relates to a process of preparing a sandwich immunoassay of NAG, which comprises (1) reacting NAG with an immobilized anti-NAG monoclonal antibody and a labeled anti-NAG monoclonal antibody to form a complex of immobilized antibody-NAG-labeled antibody and (2) detecting the activity of said reacted and unreacted labeled anti-NAG antibody.

This sandwich immunoassay is useful for diagnosis of renal disease, hepatitis, leukemia, and other such diseases. It also allows the direct and specific detection of NAG isozymes B and I in urine and blood.

11 Claims, 6 Drawing Sheets

SANDWICH IMMUNOASSAY OF β-N-ACETYLGLUCOSAMINIDASE AND MONOCLONAL ANTIBODY USED THEREIN

BACKGROUND OF THE INVENTION

1. Field of the Invention

The present invention provides a sandwich immunoassay useful for detecting β-N-acetylglucosaminidase (NAG) and a monoclonal antibody which recognizes NAG. The sandwich immunoassay comprises an immobilized anti-NAG monoclonal antibody and a labeled anti-NAG monoclonal antibody.

More particularly, the present invention provides a sandwich immunoassay for specifically detecting the presence of NAG isozyme B (and I) and a monoclonal antibody which recognizes NAG isozyme B (and I).

2. Discussion of the Background

β-N-acetylglucosaminidase (NAG or β-hexosaminidase, M.W.: approximately 120,000) is a widely distributed lysosomal enzyme, located predominantly in the renal proximal tubules. Increased NAG enzymatic activity in urine has been found to be associated with various kidney injuries. Currently, an assay for urinary NAG activity developed by Noto et al (Clin. Chem. (1983) 29, 1713) is routinely used for diagnosis and observation of rejection after renal transplantation, drug nephrotoxicity and acute renal insufficiency.

However, NAG exists as several isozymes, including A, B and I. In the urine of a normal healthy human, NAG isozyme A accounts for about 80–90% of the total isozymes while NAG isozyme B accounts for about 10–20%. NAG isozyme A is composed of two different subunits, α and β, whereas NAG isozymes B and I consist of two β-subunits. These three isozymes have different isoelectric points, substrate specificities, thermal stabilities, and other physicochemical properties.

There have been many reports describing the clinical significance of NAG isozymes. For example, the ratio of NAG isozymes B and I rises in urine of patients with renal tubular injury caused by aminoglycoside antibiotics (Gibey et al, Clin. Chim. Acta (1984) 137, 1), pyelonephritis (upper urinary-tract infection) (Vigono et al, Clin. Chim. Acta (1983) 130, 297), renal transplantation (Yuen, Clin. Chim. Acta (1987) 164, 339), and other similar disorders. The elevation of NAG isozyme I has been reported in blood of patients with hepatitis, leukemia, and other such diseases. A specific assay for NAG isozymes B and I would have increased sensitivity for the diagnosis of renal damage compared with existing assays which detect the total amount of all NAG isozymes.

The separation of NAG isozymes has been performed utilizing a variety of techniques including: ion-exchange chromatography (Ellis et al, Clin. Chim. Acta (1975) 64, 195), electrophoresis (Pitkanen et al, Enzyme (1982) 28, 14), and heat treatment (Oberketter et al, Clin. Chim. Acta (1979) 94, 281). However, these methods are difficult to adopt to routine clinical work because they are complicated, imprecise, and poorly sensitive toward NAG separation.

Recently, an enzyme immunoassay (EIA) using monoclonal antibodies specific for NAG isozyme A and B was reported (Isaksson et al, Scand. J. Clin. Lab. Invest. (1989) 49, 597–603). In this antigen capture assay, NAG is immunologically bound to an immobilized anti-NAG monoclonal antibody, and the enzymatic activity of bound NAG is measured. Unfortunately, this assay is not quantitative because the anti-NAG monoclonal antibodies inhibit the enzymatic activity of NAG.

SUMMARY OF THE INVENTION

Accordingly, one object of this invention is to provide a novel assay which is highly sensitive and quantitative for detecting the presence of NAG.

The present inventors have surprisingly discovered that by sandwiching NAG between an immobilized anti-NAG monoclonal antibody and a labeled anti-NAG monoclonal antibody it is possible to quantitatively detect NAG. The assay is more precise than previous assays because the activity of the labeled monoclonal antibody is detected rather than the enzymatic activity of NAG.

Furthermore, the inventors have discovered that by sandwiching NAG between two different monoclonal antibodies specific for NAG isozyme B, NAG isozyme B can be detected more selectively than previous methods. The inventors have also discovered that a sandwich immunoassay comprising antibodies specific for NAG isozyme B also detects the presence of NAG isozyme I making it possible to measure the total amount of NAG isozymes B and I when both are present.

The sandwich immunoassay of the present invention allows the direct and specific detection of NAG isozymes B and I in urine and blood. Thus, this invention provides a sensitive assay for renal disease, hepatitis, leukemia, and other similar diseases.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

The present invention provides a sandwich immunoassay for detecting the presence of NAG comprising the steps of:

(1) reacting an immobilized anti-NAG monoclonal antibody and a labeled anti-NAG monoclonal antibody, which recognizes a different site from that recognized by the immobilized monoclonal antibody, with a sample containing NAG so as to form a complex of immobilized antibody-NAG-labeled antibody and (2) detecting the amount of NAG present by analyzing the radioactivity or the enzymatic activity of the labeled complex.

The sandwich immunoassay of the present invention assay is preferably practiced by: (1) reacting the immobilized anti-NAG antibody with a NAG-containing sample such as a NAG standard antigen solution, urine, and blood at 4°–40° C., preferably 20°–30° C. for 0.5–24 hr, preferably 1–3 hr to form a complex of immobilized antibody-NAG, (2) reacting the complex of immobilized antibody-NAG with the labeled antibody at 4°–40° C., preferably 20°–30° C. for 0.5–24 hr, preferably 1–3 hr to form a complex of immobilized antibody-NAG-labeled antibody, and (3) detecting the activity of the labeled antibody in the complex. Alternatively, after reacting the labeled antibody with the sample to form a complex of labeled antibody-NAG, the immobilized antibody may be reacted with the complex of labeled antibody-NAG to form a complex of labeled antibody-NAG-immobilized antibody.

In the above process, the reaction of the immobilized monoclonal antibody and labeled monoclonal antibody with the sample containing NAG may be carried out either simultaneously or separately.

The sandwich immunoassay of this invention can suitably be prepared by immobilizing an anti-NAG monoclonal antibody onto a carrier to give a immobilized monoclonal antibody and labeling an anti-NAG monoclonal antibody, which recognizes a different site from that recognized by the immobilized monoclonal antibody, with a radioisotope or an enzyme to give a labeled monoclonal antibody.

Suitable anti-NAG isozyme B monoclonal antibodies useful in accordance with the present invention include monoclonal antibodies which are specific for NAG isozyme B, preferably monoclonal antibodies Hex 31 and Hex 32 produced by hybridomas Hex 31 and Hex 32, respectively, are used. Hybridoma Hex 31 and Hybridoma Hex 32 were deposited on May 20, 1992 with the Fermentation Research Institute at 1-3, Higashi 1-chome, Tsukuba-shi, Ibaraki-ken, 305, Japan in accordance with the Budapest Treaty as "Mouse hybridoma Hex 31", accession No FERM BP-3858 and "Mouse hybridoma Hex 32", accession No. FERM BP-3859, respectively.

Preferably, Hex 31 is used as the immobilized antibody and Hex 32 is used as the labeled antibody. However, the inverted combination can alternatively be used.

Additionally, monoclonal antibodies Hex 31 and Hex 32 can suitably be combined with other monoclonal or polyclonal antibodies which also recognize NAG isozyme B and I.

Considering that both NAG isozymes B and I can be detected by the present sandwich immunoassay and further that NAG isozymes B and I consist of two β-subunits structurally differing in only attached sugar chains, the inventors believe that the anti-NAG isozyme B monoclonal antibodies of this invention recognize the β-subunits without any sugar chains.

Suitable anti-NAG monoclonal antibodies in accordance with the present invention can be prepared from the hybridomas by conventional methods. For example, NAG, preferably NAG isozyme B, in an amount sufficient to promote formation of antibodies, is emulsified in an adjuvant such as Freund's complete adjuvant. The NAG used as an immunogen may be either crude or partially purified. Purified NAG isozyme B, which is purified using anti-NAG isozyme B monoclonal antibody, preferably monoclonal antibody Hex 33 is used. Hybridoma Hex 33 has been deposited with Fermentation Research Institute at 1-3, Higashi 1-chome, Tsukuba-shi, Ibaraki-ken, 305, Japan as "Mouse hybridoma Hex 33" with accession No. FERM BP-3860 since May 20, 1992 under the conditions of the Budapest Treaty. The emulsion can suitably be is intramuscularly inoculated into mice repeatedly at intervals of a few months.

3 to 5 days following the last immunization, the spleens of the mice can be collected. Myeloma cells having a suitable marker such as 8-azaguanine resistance can be used as parent cells which are fused with the antibody-producing cells to prepare hybridomas. Suitable media use for the preparation of hybridomas according to the present invention include media such as Eagle's MEM, Dulbecco's modified medium, and RPMI-1640. Myeloma parent cells and spleen cells can be suitably fused at a ratio of approximately 1:5. Polyethylene glycol (PEG) can be used as a suitable fusing agent, preferably at a concentration of 50% for efficient fusion. Resulting cells were selected by the HAT method (Littlefield, J. W., Science (1964) 145:709.)

Screening of obtained hybridomas can suitably be performed by conventional methods including an immunoassay using culture supernatant of the hybridomas to give a clone of hybridoma producing objective immunoglobulin. The antibody-producing hybridoma obtained can be cloned a few times using known methods such as the limiting dilution method.

In order to produce the anti-NAG monoclonal antibodies of the present invention, the hybridoma obtained above is cultured either in vitro or in vivo. If the hybridoma is cultured in vitro, the hybridoma is cultured in the above-mentioned media supplemented with fetal calf serum (FCS) for 3–5 days and monoclonal antibodies are recovered from the culture supernatant. If the hybridoma is cultured in vivo, the hybridoma is implanted in the abdominal cavity of a mammal, and after 1-3 weeks the ascitic fluid is collected to recover monoclonal antibodies therefrom. Much larger quantities of the monoclonal antibodies can efficiently be obtained using in vivo cultures than in vitro cultures, thus the in vivo cultures are preferably used.

The monoclonal antibody obtained from the supernatant or ascitic fluids can be purified by conventional methods such as ammonium sulfate-fractionation, Protein G-Sepharose column chromatography, or their combinations.

The sandwich immunoassay of NAG can suitably be prepared using an immobilized anti-NAG antibody and a labeled anti-NAG antibody. Anti-NAG antibodies according to the present invention can Suitably be immobilized on commercially available carriers for the antigen-antibody reaction including beads, balls, tubes, and plates made of glass or synthetic resin. Suitable synthetic resins include polystyrene and polyvinyl chloride. Anti-NAG antibodies are suitably adsorbed onto the carrier by allowing them to stand at room temperature overnight in phosphate buffer at pH 6-10, preferably about pH 7.0. The immobilized anti-NAG antibody can be stored cold in the presence of preservatives such as sodium azide. Both monoclonal and polyclonal antibodies can be immobilized onto carriers using this method.

Labeled anti-NAG antibodies in accordance with the present invention can suitably be prepared by labeling anti-NAG antibodies with any substance commonly used for an immunoassay including radioisotopes, enzymes, and fluorescent substances. Radioisotopes and enzymes are preferably used. When radioisotopes are used as labels, the antibody is preferably labeled with $^{125}$I using conventional methods such as the Chloramine T method (Hunter et al, Nature (1962) 194:495). When enzymes are used as labels, the antibody is labeled with an enzyme such as horseradish peroxidase, $\beta$-D-galactosidase, or alkaliphosphatase by conventional methods including the maleimido method and the Hingi method (Ishikawa et al, J. Immunoassay (1983)4:1).

The activity of the label can be detected by conventional methods. If radioisotopes are used as labels, the activity of the label can be detected using an appropriate instrument such as a scintillation counter. If enzymes are used as labels, the activity of the label can be detected by measuring absorbance, fluorescence intensity, or luminescence intensity after reacting the enzyme with a appropriate substrate.

The present invention also provides a kit for assaying the amount of NAG present in a sample of NAG. The kit of the present invention comprises an immobilized anti-NAG monoclonal antibody and a labeled anti-NAG monoclonal antibody. When NAG is assayed using this kit, NAG becomes sandwiched between the immobilized monoclonal antibody and the labeled monoclonal antibody. When monoclonal antibodies Hex 31 and Hex 32 are used in the kit of present invention, the presence of NAG isozyme B (and I) is quantitatively and specifically detected.

Suitably, the kit contains immobilized anti-NAG isozyme B monoclonal antibodies and labeled anti-NAG isozyme B monoclonal antibodies, preferably monoclonal antibody Hex 31 and Hex 32 (produced by Hybridoma Hex 31 and Hex 32, respectively, as described before) are used. In a preferred embodiment, Hex 31 is used as the immobilized antibody and Hex 32 is used as the labeled antibody. However, the inverted combination can alternatively be used. Further, Hex 31 or Hex 32 can be combined with another monoclonal or polyclonal antibody which recognizes different site of NAG isozyme B from that recognized by Hex 31 or Hex 32.

Since the monoclonal antibodies useful for this kit can recognize both NAG isozyme B and I when they coexist, the total amount of NAG isozymes B and I can be measured by this invention.

Having generally described this invention, a further understanding can be obtained by reference to certain specific examples which are provided herein for purposes of illustration only and are not intended to be limiting unless otherwise specified.

EXAMPLES

Sandwich RIA of NAG (1) Preparation of hybridoma producing anti-NAG monoclonal antibody and production of the antibody.

(a) Immunization

Using partially purified $\beta$-N-acetylglucosaminidase isozyme B from human placenta (Sigma Chemical Co.) as an immunogen, Balb/c mice (4 weeks) were immunized according to the following procedure:

The enzyme was centrifuged at 1,200 rpm for 5 min to obtain a precipitate. The resulting precipitate was dissolved in physiological saline and mixed with Freund's complete adjuvant. The enzyme (10 μg/mouse) was intraperitoneally injected into mice. Subsequently, the mice received three intramuscularly injections of the same amount of the enzyme at 2-month intervals.

(b) Cell fusion

Four days after the last injection, a titer of antiserum, collected from immunized mice, was measured according to the procedure in item (c) below. Spleens having significant titer were excised from the mice. The splenic cells were allowed to stand in 0.17M ammonium chloride at freezing point for 5 min to destroy erythrocytes. The remaining cells were suspended in RPMI 1640 medium to give splenic lymphocytes useful in cell fusion. A mixture of myeloma cells ($6.3 \times 10^1$ cells) resistant to 8-azaguanine suspended in RPMI 1640 medium and the splenic lymphocytes (X63.653, $3.5 \times 01^8$ cells) was centrifuged. The resulting supernatant was removed. To the cell precipitate was added by pipet 0.8 ml of 50% polyethylene glycol (M.W. 4, 000, Merck) in 1 min with stirring. The mixture was stirred for an additional 1.5 min. To the mixture was added 2 ml of RPMI 1640 medium in 2 min and then 2 ml of that in 1 min. Finally, 18 ml of RPMI 1640 medium was added dropwise with gentle agitation.

After centrifugation, the resulting supernatant was removed. The cell precipitate was suspended in 100 ml of HAT medium (20% FCS-RPMI 1640 medium supplemented with $1 \times 10^{-4}$ M hypoxanthine, $4 \times 10^{-7}$M aminopterin, and $1.6 \times 10^{-5}$M thymidine) and the suspension (0.1 ml/well) was seeded in twelve 96-well tissue culture plates (Falcon). To each well was added 50 μl and 100 μl of HAT medium after 2 days and 7 days, respectively. After 10 days, the culture supernatant was collected and subjected to screening by the method described in item (c) below. The hybridomas which produced anti-NAG antibodies were cloned three times by the "limiting dilution method" to give hybridoma Hex 31, Hex 32, and Hex 33.

(c) Measurement of titer of antibody

Microtiter plate (Dynatech Lab. Inc.) was coated with rabbit anti-mouse IgG (10 μg/100 μl/well) in PBS (10 mM phosphate buffer containing 0.15M sodium chloride, pH 7.4) and left at 4° C. overnight. The wells were washed once with PBS containing 1% bovine serum albumin (BSA) and incubated with the same buffer (200 μl/well) at 37° C. for 1 hr. After the wells were washed three times with PBS containing 0.05% Tween 20, 100 μl of the antiserum or the culture supernatant, containing hybridoma, was added to the wells and incubated at room temperature for 2 hr. After washing three times, partially purified NAG isozyme A or B from human placenta (Sigma Chemical Co.) (0.5 mU/100 μl) in PBS containing 0.1% BSA was added and incubated at room temperature for 2 hr. After washing three times, 1 mM 4-methylumbelliferyl-2-acetamide-2-deoxy-$\beta$-D-glucopyranoside in 50 mM citrate-phosphate buffer, pH 4.9 (100 $\mu$l) was added and incubated at 37° C. for 2 hr (enzyme reaction). The enzyme reaction was stopped by addition of 0.5M glycine-NaOH, pH 10.5 (100 $\mu$l). The fluorescence intensity of 4-methylumbelliferone released in each well was measured at an excitation wavelength of 365 nm and an emission wavelength of 450 nm, using a microplate-reader (MTP-32, Corona Electric Co, Ltd.).

(d) Preparation of ascitic fluid:

Hybridoma Hex 31 or Hex 32 (2×10¹ cells) was injected intraperitoneally into mice to which 0.2 ml of pristan had been injected intraperitoneally 21 days before. The ascitic fluid was collected after 1–3 weeks, centrifuged to remove cells therein, and preserved at −80° C.

(e) Purification of monoclonal antibody and Confirmation of titer of the antibody:

The ascitic fluid (20 ml) preserved at −80° C. was melted, diluted twice with the same volume of PBS, and then loaded onto a Protein G Sepharose 4 Fast Flow column (1.5×13 cm, Pharmacia) equilibrated with 20 mM phosphate buffer, pH 7.0 (abbreviated as Buffer A, hereinafter). After washing the column with 60 ml of Buffer A, mouse IgG was eluted with 10 mM glycin-HCl buffer, pH 2.7 (60 ml). The eluate was neutralized with 1M Tris and then treated with 50% ammonium sulfate at 0° C. After centrifugation at 6,000 rpm for 30 min, the resulting precipitate was dissolved in 10 ml of PBS and dialyzed at 4° C. overnight against PBS to give purified antibody.

Figure 1A:
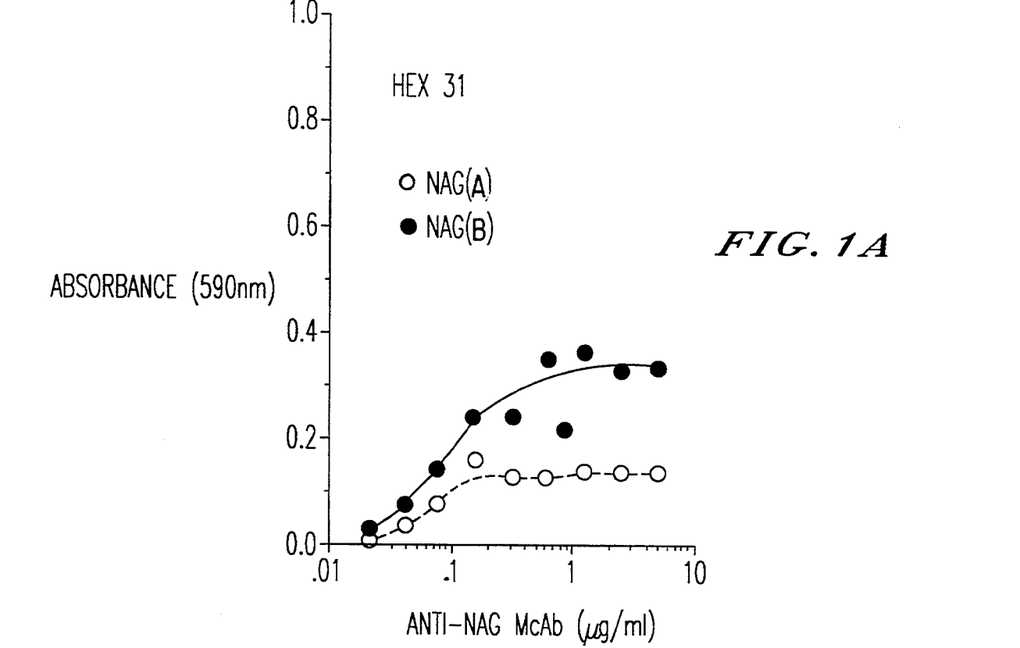
FIG. 1(A) Titer of monoclonal antibody Hex 31 at various concentration to NAG isozyme A (-○-) and B (-●-).
Figure 1B:
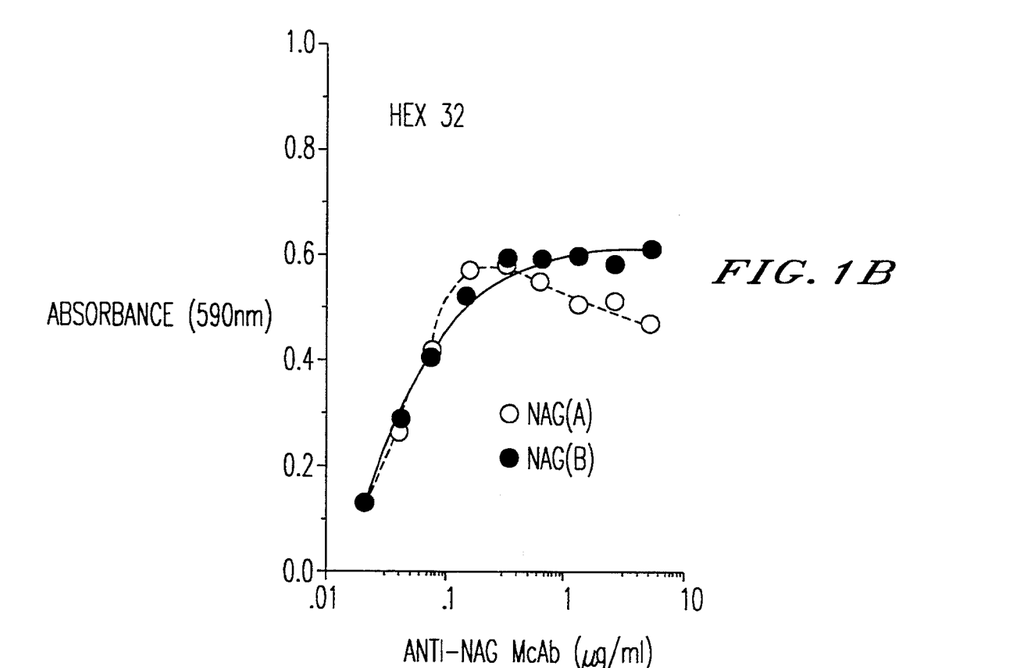
FIG. 1(B) Titer of the monoclonal antibody Hex 32 at various concentration to NAG isozyme A (-○-) and B (-●-).

A confirmation of the titer on the purified antibody was carried out according to the method described above in item (c); the enzyme reaction was performed for 30 min using sodio-m-cresolsulfonphtaleinyl-N-acetyl-$\beta$-D-glucosaminide as a substrate and the absorbance was determined at 590 nm. As a result, the antibodies had significant titer even at a concentration of 0.1 $\mu$g/ml as shown in FIGS. 1A and 1B. Both monoclonal antibody Hex 31 and Hex 32, reacted very well with NAG isozyme B (-●-); slight cross-reactivity to NAG isozyme A was observed (○).

(f) Typing of antibody

An isotype determination of the immunogloblin produced by the hybridoma was carried out by the enzyme immunoassay method using an Isotyping Kit (Phar Minigen). The results showed that both anti-human NAG monoclonal antibodies Hex 31 and Hex 32 belong to IgG$_1$.κ.

Figure 2A:
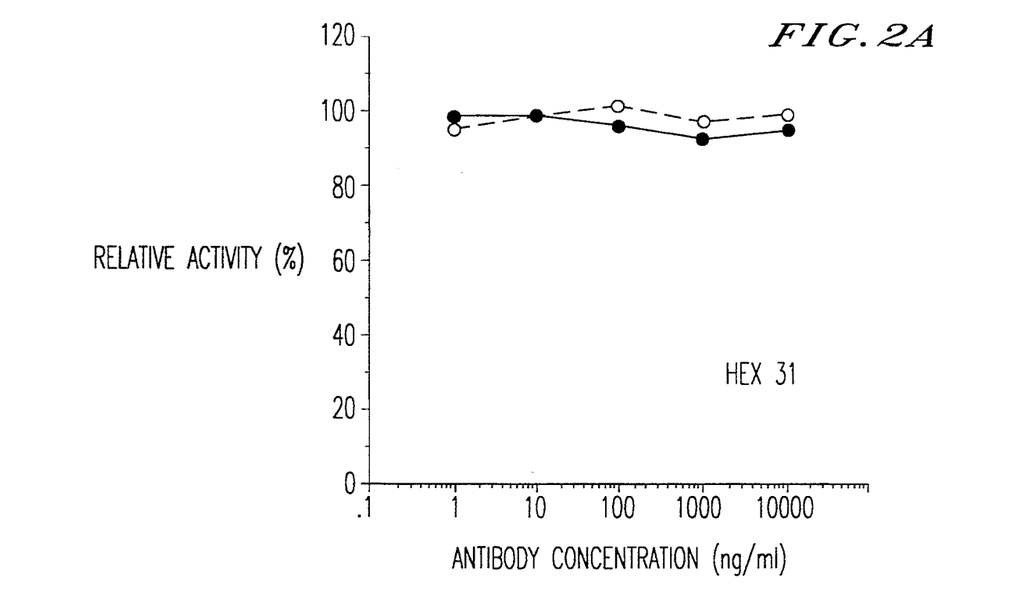
FIG. 2(A) Enzymatic activity of NAG isozyme A (-○-) and B (-●-) after binding to monoclonal antibody Hex 31 at various concentrations.
Figure 2B:
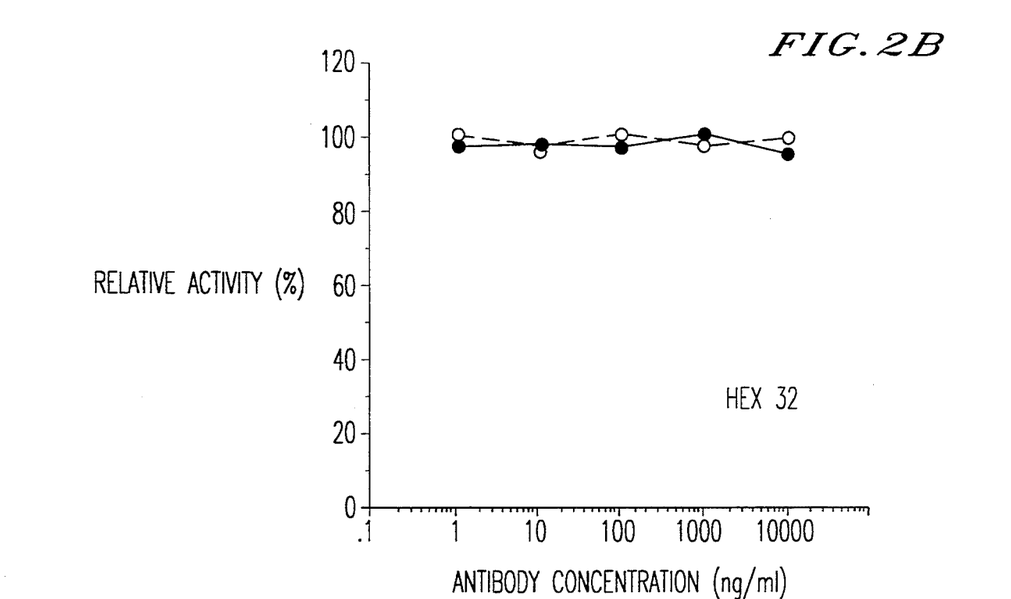
FIG. 2(B) Enzymatic activity of NAG isozyme A (-○-) and B (-●-) after binding to the present monoclonal antibody Hex 32 at various concentrations.

(g) Inhibition of enzymatic activity of NAG by antibody:

Using 0.1% BSA-containing PBS, 110U/L NAG isozyme A or B and 0.1–10,000 ng/ml anti-human NAG monoclonal antibody Hex 31 or Hex 32 were prepared, and reacted at room temperature for 2 hr. After the reaction, the enzymatic activity of NAG was measured using NAG Test Shionogi (Shionogi & Co. Ltd.). As shown in FIG. 2, the enzymatic activities of NAG isozyme A (-○-) and B (-●-) were not inhibited at all even by an excess of antibodies. Thus, the present monoclonal antibody does not inhibit enzymatic activity of NAG and therefore must recognize a different site on NAG than the site recognized by Isaksson's monoclonal antibody.

(2) Sandwich immunoassay of NAG (a) Radioisotopic labelling

In 0.5M phosphate buffer, pH 7.5 (50 $\mu$l, abbreviated as Buffer B, hereinafter) was dissolved 25 $\mu$g of purified antibody Hex 32, to which 0.5 mCi Na $^{125}$I (5 $\mu$l/25 $\mu$l) and Chloramine T (50 $\mu$g/25 $\mu$l) in Buffer B were added. Reaction was allowed to proceed at room temperature for 15 sec. The reaction was stopped by addition of sodium disulfite (100 $\mu$g/25 $\mu$l) in Buffer B and potassium iodide (2.5 mg/20 $\mu$l) in water. The reaction solution was loaded onto PD-10 column (Pharmacia) equilibrated with PBS containing 0.5% BSA and 0.1% sodium azide to collect fractions which included the labeled antibody.

(b) Sandwich RIA

Microtiter plate (Dynatech) were coated with purified antibody Hex 31 (1 $\mu$g/100 $\mu$l/well) in PBS and stored at 4° C. overnight. The wells were washed once with PBS containing 1% BSA and incubated with the same buffer (200 $\mu$l/well) at 37° C. for 1 hr. The wells were washed three times with PBS containing 0.05% Tween 20, and then 75 $\mu$l of 0.2M citrate-phosphate buffer (pH 5.0) containing 0.1% BSA and 0.02% sodium azide, followed by the addition 25 $\mu$l of standard antigen solution or urinary sample to the wells. The samples were incubated at room temperature for 2 hr (1st reaction). Next, after washing the wells three times, $^{125}$I-labeled Hex 32 (c.a. 10⁵ cpm/10 ng/100 $\mu$l) in 0.2M citrate-phosphate buffer (pH 7.0) containing 0.1% BSA and 0.02% sodium azide was added. Samples were allowed to stand at room temperature for 2 hr (2nd reaction). After the reaction, the wells were washed three times and cut out; the radioactivity of each well was determined with a $\gamma$-counter (ARC-600, Aloca).

Partially purified human placental NAG isozyme A or B (Sigma Chemical Co.) (0.5–20 U/L as enzymatic activity) was used as the standard antigen solution.

The optimal pH for the 1st and 2nd reactions in the above-mentioned sandwich RIA was determined using 0.2M citrate-phosphate buffer (pH 4.5–8.0) containing 0.1% BSA and 0.02% sodium azide according to the method described below:

The pH of the 2nd reaction was first fixed at 7.0; the pH of the 1st reaction was then varied. The cross-reactivity to NAG isozyme A amounted to 33% at pH 7.0, however it reduced as the pH of 1st reaction fell, so that it amounted to 15% at pH 5.0 (it appeared that the 15% cross-reactivity was not due to NAG isozyme A, but NAG isozyme I contaminating the standard antigen solution of NAG isozyme A as described below). At pH 4.5, no reactivity to both NAG isozyme A and B was observed.

Next, the pH of 1st reaction was fixed at pH 5.0 and the pH of the 2nd reaction was varied. No change in the cross-reactivity to NAG isozyme A (13–17%) was observed. The effects of pHs in the 1st and 2nd reaction upon the reactivity to NAG isozymes appeared to be due to the characteristic of the immobilized antibody Hex 31 and the labeled antibody Hex 32, respectively. From the above results, a pH of 5.0 for the 1st reaction was selected to decrease the observed cross-reactivity to NAG isozyme A, and pH 7.0 for the 2nd reaction was used to increase the sensitivity of the test.

Figure 3:
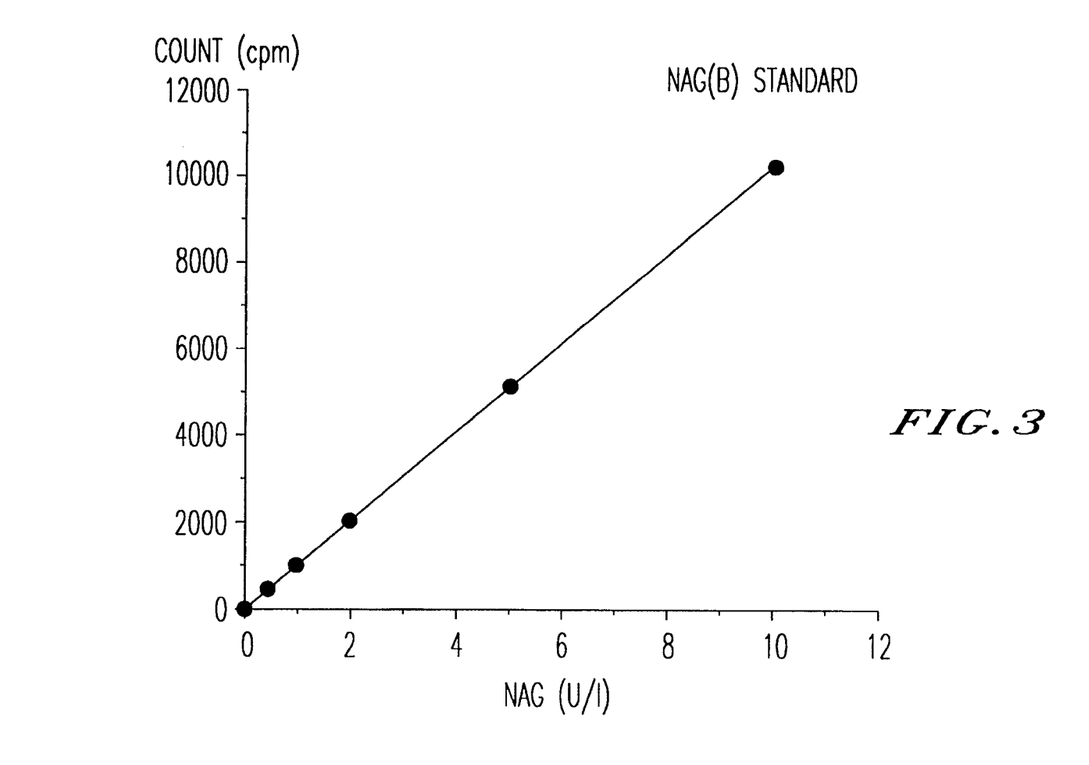
FIG. 3 Standard calibration curve of the sandwich RIA using NAG isozyme B as a standard antigen.

A standard calibration curve of the sandwich RIA using NAG isozyme B as a standard antigen is shown in FIG. 3. It displays excellent linearity over the range from 0 to 10 U/L.

The reproducibility of the RIA is shown below in Table 1. The estimation was performed using the standard antigen solution and eight urine samples. The coefficients of variation (C.V.) of the within-assay series were less than 10% (n=5).

Sandwich EIA of NAG

TABLE 1

|  | 1 | 2 | 3 | 4 | 5 | AVG | sp | SD | CV (%) | RIA |
|---|---|---|---|---|---|---|---|---|---|---|
| NAG (B) | | | | | | | | | | |
| 0 | 286 | 327 | 300 | 364 | 323 | 320 | 0 | 27 | 8.33 | |
| 0.5 | 915 | 945 | 932 | 878 | 920 | 918 | 598 | 23 | 2.45 | |
| 1 | 1371 | 1468 | 1411 | 1379 | 1434 | 1413 | 1093 | 36 | 2.53 | |
| 2 | 2384 | 2299 | 2254 | 2660 | 2660 | 2451 | 2131 | 175 | 7.15 | |
| 5 | 4773 | 5573 | 5344 | 6195 | 6065 | 5590 | 5270 | 514 | 9.19 | |
| 10 | 10616 | 10916 | 10249 | 10261 | 10641 | 10537 | 10217 | 253 | 2.40 | |
| urine | | | | | | | | | | |
| 8 | 1135 | 1196 | 1227 | 1237 | 1209 | 1201 | 881 | 36 | 2.98 | 0.79 |
| 4 | 1796 | 1548 | 1790 | 1642 | 1714 | 1698 | 1378 | 94 | 5.52 | 1.27 |
| 11 | 1588 | 1626 | 1672 | 1625 | 1549 | 1612 | 1292 | 41 | 2.56 | 1.19 |
| 7 | 2196 | 1991 | 2169 | 2062 | 2051 | 2094 | 1774 | 77 | 3.67 | 1.66 |
| 27 | 3793 | 3653 | 4096 | 3662 | 3657 | 3772 | 3452 | 170 | 4.51 | 2.84 |
| 26 | 2291 | 2320 | 2457 | 2213 | 2159 | 2288 | 1968 | 102 | 4.45 | 1.84 |
| 64 | 4914 | 5245 | 5255 | 5235 | 4949 | 5120 | 4800 | 154 | 3.01 | 3.70 |
| 29 | 4052 | 4300 | 4208 | 4467 | 4284 | 4262 | 3942 | 135 | 3.16 | 3.15 |

(3) Analysis of NAG isozymes by ion-exchange chromatography:

The specificity of the present sandwich RIA to NAG isozymes was examined by the ion-exchange chromatography method. The separation of NAG isozyme was performed by FPLC system (Pharmacia) using Mono Q column (0.5×5.0 cm). The elution was done with 10 mM phosphate buffer (pH 6.0) at a flow rate of 1 ml/min according to the "linear concentration gradient method". The amount of NAG in the resulting fractions was measured by both the present RIA and enzyme assay using NAG Test Shionogi (Shionogi & Co. Ltd.); sodio-m-cresolsulfonphtaleinylN-acetyl-$\beta$-D-glucosaminide was used as a substrate.

As a sample for the analysis of NAG isozymes, partially purified NAG isozyme A or B from human placenta (Sigma Chemical Co.) and urinary samples, concentrated 5 to 10-fold, were used. Those samples were dialyzed at 4° C. overnight against 10 mM phosphate buffer (pH 6.0) and then injected into column after adding 0.1% BSA as a carrier protein.

Figure 4A:
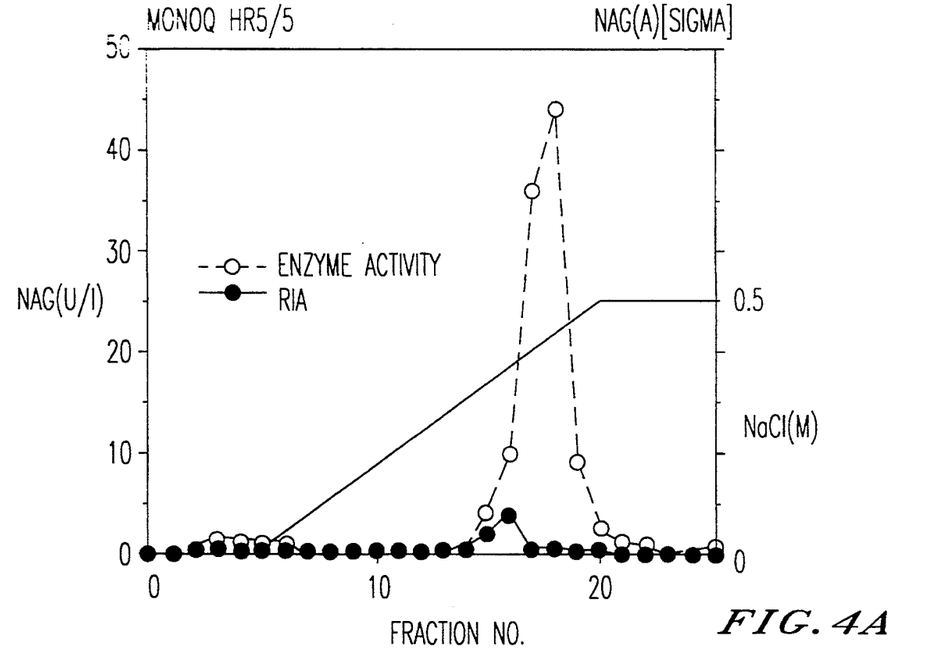
FIG. 4(A) Ion-exchange chromatography of partially-purified NAG isozyme A from human placenta. Fractions were subjected to the sandwich RIA (-●-) and enzyme assay (-○-).

As shown in FIG. 4(A) (the elution pattern of NAG isozyme A from human placenta), the peak of fraction No. 16 of the RIA (-●-) appeared faster than that of the enzyme assay (-○-). The peak was probably due to NAG isozyme I contaminating partially purified NAG isozyme A as an antigen because (1) as two anti-NAG isozyme B monoclonal antibodies were used in this RIA, the selectivity of the RIA to NAG isozyme B was very high and the possibility of the cross-reactivity to isozyme A having quite different subunits from isozyme B is negligible, (2) as NAG isozyme I is composed of two $\beta$-subunits as well as isozyme B, and differs from NAG isozyme B in only sugar chain, it is possible that the monoclonal antibodies used in this RIA recognize NAG isozyme I as well as isozyme B.

Figure 4B:
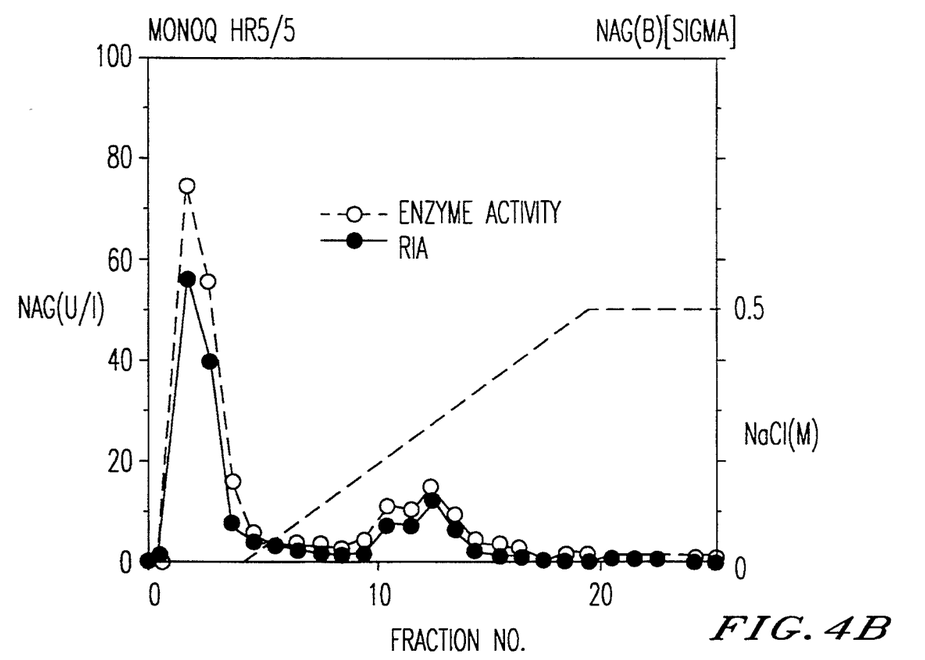
FIG. 4(B) Ion-exchange chromatography of partially-purified NAG isozyme B from human placenta. Fractions were subjected to the sandwich RIA (-●-) and enzyme assay (-○-).
Figure 5A:
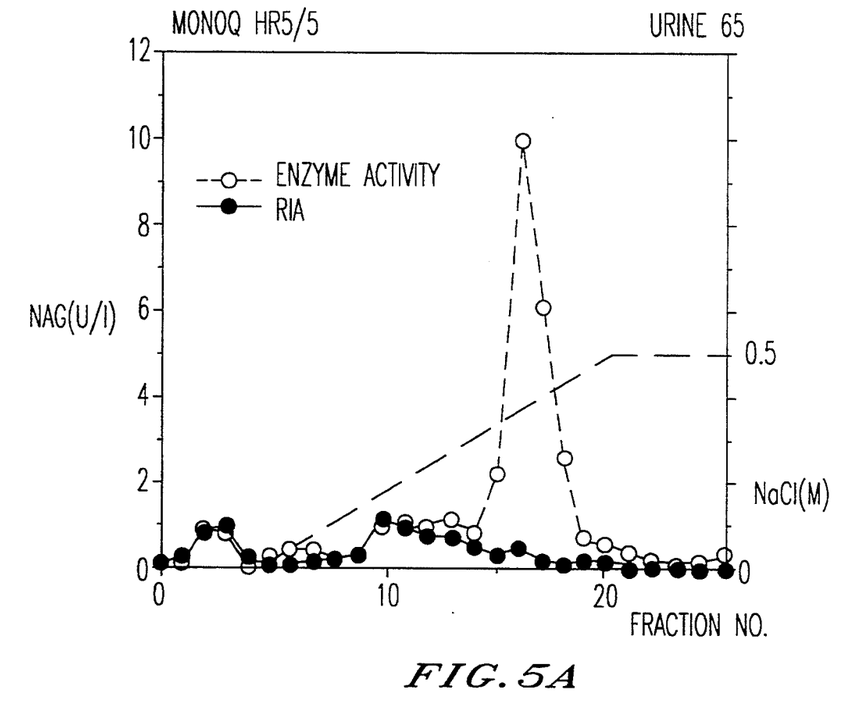
FIG. 5(A) & FIG. 5(B) Ion-exchange chromatography of NAG isozymes in urine samples. Fractions were subjected to sandwich RIA (-●-) and enzyme assay (-○-).
Figure 5B:
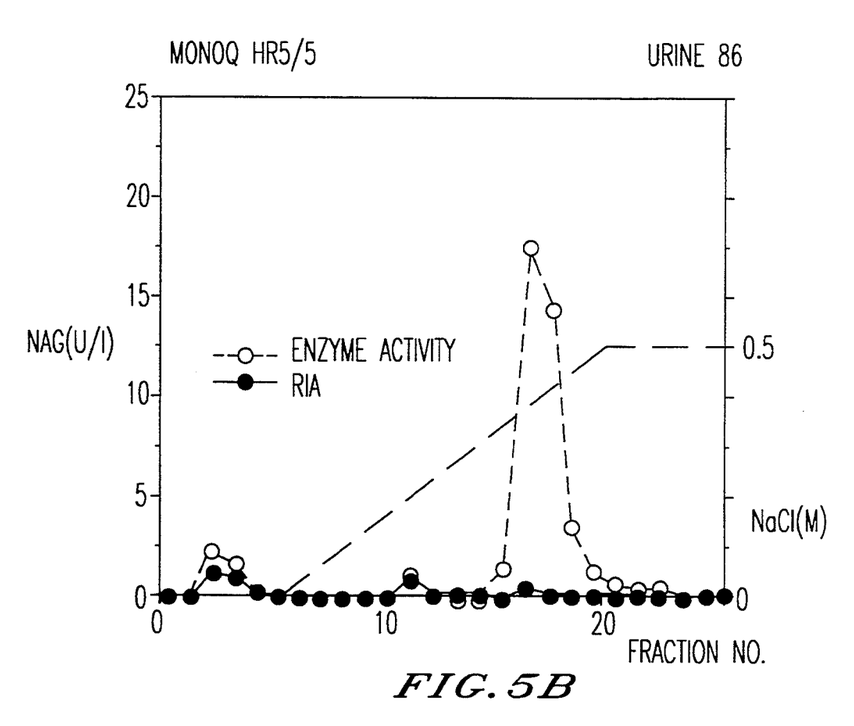

As shown in FIG. 4(B), the elution pattern of NAG isozyme B from human placenta by the RIA was identical to that of the enzyme assay, in which patterns appeared peaks (fraction No. 11-13) due to contamination of isozyme I. In the case of the elution patterns of two urinary samples (FIGS. 5A and 5B), the peaks due to NAG isozyme A (fraction No. 16), B (fraction No. 2-4), and I (fraction No. 10-11) appeared in the enzyme assay, but there is no peak due to isozyme A in the present RIA. These results indicate that the amount of NAG detected by the RIA reflected those of isozymes B and I.

(1) Purification of NAG isozyme B from human placenta

The purification of NAG isozyme B used as an antigen comprised the following steps: 1) ammonium sulfate-fractionation, 2) adsorption of glycoprotein by Con A-Sepharose (Pharmacia) chromatography, 3) separation of NAG isozyme B from NAG isozymes by antibody-column chromatography using monoclonal antibody Hex 33 obtained in the above item 1.(1) (b) and by Mono Q column (Pharmacia) chromatography, and finally 4) purification by Sephacryl S-200 (Pharmacia). The anti-NAG antibody-column was prepared according to Schneider's method (J. Biol. Chem. 257, 10766–10769, 1982). The enzymatic activity of NAG was measured by the NAG Test Shionogi (Shionogi & Co., Ltd.) using sodio-m-cresolsulfonphtaleinyl-N-acetyl-$\beta$-D-glucosaminide as a substrate. The detailed procedure was described below (all operations in the procedure were carried out at 4° C.).

Twelve human placenta without funiculus umbilicals and capsula were washed repeatedly with distilled water to remove erythrocyte; they were cut into pieces, and then homogenized with 25 mM sodium phosphate buffer, at pH 6.0 using twice the initial volume. The homogenate was centrifuged at 10,000×g for 20 min. The resulting precipitate was dissolved in 50 mM sodium phosphate buffer containing 0.3M sodium chloride, pH 7.0 (abbreviated as buffer C, hereinafter) and dialyzed against the same buffer. After stirring slowly overnight with Con A-Sepharose (40 ml) equilibrated with Buffer C, the Con A-Sepharose was filtered on a glass-filter and filled up in a column (2.6×46 cm). The column was washed with three times volume of Buffer C and then eluted with Buffer C containing $\alpha$ methyl-mannoside to give fractions having enzymatic activity of NAG. The fractions were dialyzed against Buffer C. After the resultant was added to a Protein G-Sepharose column (1.5×12 cm, Pharmacia), equilibrated with Buffer C, wherein passing fractions were loaded onto an antibody-column (2.8×3 cm) equilibrated with Buffer C, and then washed with Buffer C, followed by elution with 0.2M glycine-HCl buffer, pH 3.0.

The eluate was immediately neutralized with 0.5M sodium phosphate buffer, pH 7.5 and dialyzed against 0.01M sodium phosphate buffer, pH 6.0 (abbreviated as Buffer D, hereinafter). This solution was concentrated with Collodion Bag (Sartorius) and passed through a Mono Q column (0.5×5 cm). A passing fraction, containing NAG isozyme B, which was not adsorbed to Mono Q column was collected, concentrated, and loaded onto Sephacryl S-200 column (2.6×73 cm) having been equilibrated with Buffer D containing 0.1M sodium chloride. Fractions having enzymatic activity were collected to give an objective enzyme (NAG isozyme B) (c.a. 2.3 mg). NAG isozyme A separated by Mono Q column was also purified by Sephacryl S-200 to give 3.5 mg of isozyme. The purity of these NAG isozymes was confirmed by separating these proteins by electrophoresis technique using SDS-PAGE gradient gel (Daiichi Pure Chemicals Co., Ltd.) and visualization with Coomassie brilliant blue.

As a result, under the non-reducing condition two bands of 56K ($\alpha$ chain) and 60K ($\beta$ chain) appeared in the case of NAG isozyme A, only one bands of 60K ($\alpha$ chain) appeared in case of NAG isozyme B.

Under reducing condition, the 60K band separated to two bands of 30K ($\beta$ a chain) and 28K ($\beta$ b chain); the 62 chain of NAG isozyme A and B was made low molecule. The band of $\alpha$ chain of NAG isozyme A was unchanged.

The purity of the $\beta$ chain of NAG isozyme B under non-reducing condition was examined by densitometer. NAG isozyme B was found to be well purified.

(2) Preparation of enzyme-labeled antibody

Using horseradish peroxidase as an enzyme, an enzyme-labeled antibody was prepared by the hinge method.

To an anti-NAG monoclonal antibody Hex 32 (18 mg) purified in above item 1.(1)(e) was added pepsin (878 $\mu$g/8.8 ml, Biehringer Mannheim) in 0.1M citrate buffer, pH 4.1 and reacted at 37° C. for 18 hr to digest the antibody. The reaction mixture was separated by a Superose 12 column (1.5×50 cm, Pharmacia). The obtained F(ab')$_2$ fraction was concentrated to 2.2 ml by Centricon 30 (Amicon) and reduced at 37° C. for 90 min with 0.1M 2-mercaptoethylamine (1/10 volume) in 0.1M phosphate buffer (pH 6.0) containing 5 mM ethylenediaminetetraacetic acid (EDTA). The resulting Fab' fraction was separated by Superose 12 column (1.5×50 cm) equilibrated with the same buffer and concentrated to 1 ml by Centricon 10.

To peroxidase (1.65 mg/2.47 ml, Sigma Chemical Co.) in 0.1M phosphate buffer, pH 7.0 was added $\epsilon$-maleimidocaproyloxysuccinimide (EMCS) (13.1 mg/164, $\mu$l, Dojin) in N,N-dimethylformamide and reacted at 30° C. for 30 min. The reaction mixture was centrifuged to remove precipitate. The resulting supernatant was subjected to PD-10 column equilibrated with 0.1M phosphate buffer (pH 6.0) to remove low molecule substances. Maleimidated-peroxidase thus obtained was reacted with Fab' fragment at 4° C. for 15 hr at a mole ratio of 1:1. The resulting peroxidase-labeled anti-NAG monoclonal antibody (Fab' fragment) was separated from reaction mixture by Superose 12 column (1.5×50 cm) equilibrated with 0.1M phosphate buffer (pH 6.5) to yield 3.8 mg of the labeled antibody.

(3) Preparation of antibody-coated plate

Immunomodule Plate F-SH (Nunc) was coated with anti-NAG monoclonal antibody Hex 31 (10 $\mu$g/ml, 200 $\mu$l/well) in 10 mM PBS (pH 7.4) at 4° C. for 24 hr. The wells were washed three times with 10 mM PBS (pH 7.4) containing 0.05% Tween 20, to which was added 10 mM PBS, pH 7.4 (300 $\mu$l/well) containing 10% saccharose and 10% BSA (Sigma Chemical Co.). The solution was allowed to stand at room temperature for 1 hr. After removing the buffer from the wells, the plate was dried overnight under reduced pressure with silica gel in a desiccator to give an antibodycoated plate.

(4) Sandwich EIA

The antibody-coated plate prepared in item (3) was washed once with 10 mM phosphate buffer, pH 7.4 (300 $\mu$l/well) containing 0.05% Tween 20, 0.15M sodium chloride, and 0.06% Kathon CG (Rohm and Haas). To each well was added 150 $\mu$l of 0.4M citrate buffer, pH 5.2 containing 0.1% BSA and Kathon CG and 25 $\mu$l of standard antigen solution (0–80 ng/ml NAG isozyme B purified in above item 2.(1) in 10 mM phosphate buffer, pH 6.0 containing 0.1% BSA, 0.1% Kathon CG and 0.15M sodium chloride) or urinary sample. After agitation, a 1st reaction was carried out at 30° C. for 2 hr, followed by washing four times.

To each well was added 100 $\mu$l of labeled antibody solution (250 ng/ml labeled antibody prepared in above item 2.(2) in 10 mM phosphate buffer, pH 7.4 containing 0.1% BSA, 0.1% Kathon CG and 0.15M sodium chloride), and 2nd reaction was carried out at 30° C. for 1 hr. After washing four times, 100 $\mu$l of substrate solution (4.3 mM 2,2'-azinobis 3-ethylbenzthiazoline-6-sulfate (ABTS) in 10 mM citrate buffer, pH 5.0 containing 2 mM hydrogen peroxide) was added to each well and the enzyme reaction was carried out at 30° C. for 15 min. The enzyme reaction was stopped by adding 100 $\mu$l of 10 mM citrate buffer, pH 5.0 containing 0.05% sodium azide. The absorbance was detected at 415 nm using a microplatereader (MTP-32, Corona Electric Co., Ltd.). The amount of NAG isozyme B in urinary sample was determined from the standard curve.

(a) Standard curve and Cross-reactivity to NAG isozyme A

Figure 6:
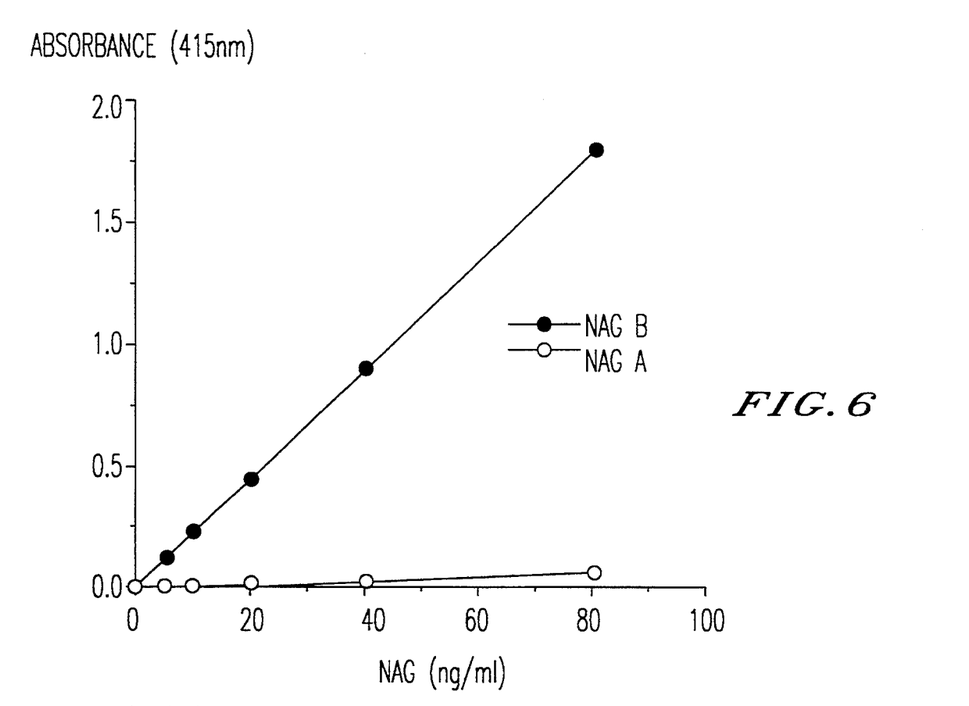
FIG. 6 Standard calibration curve of sandwich EIA using NAG isozymes B (-●-) and A (-○-) as a standard antigen.

Standard curve of the present sandwich EIA using NAG isozyme B as a standard antigen was shown in FIG. 6 (-●-). It displayed excellent linearity over the range from 0 to 80 ng/ml. The mean +3SD as the lower limit of detection was 0.5 ng/ml (n=20). Furthermore, this sandwich EIA was carried out using NAG isozyme A or bovine NAG as a standard antigen. As a result, the cross-reactivity to NAG isozyme A (-○-) amounted to 2–3%; there was no cross-reactivity to bovine NAG.

(b) Reproducibility

The reproducibility of the present sandwich EIA is shown below in Table 2. The estimation was done using three urinary samples having different concentration. The within-assay C.V. was 2.5–5.4% and the between-assay C.V. was 6.2–9.1%.

TABLE 2

| Assay | Precision of the Present EIA | | | |
|---|---|---|---|---|
| | n | Mean, ng/ml | SD, ng/ml | CV, % |
| Within-assay | | | | |
| urine 1 | 8 | 5.7 | 0.3 | 5.4 |
| urine 2 | 8 | 20.0 | 0.5 | 2.5 |
| urine 3 | 8 | 37.1 | 1.8 | 4.8 |
| Between-assay[a] | | | | |
| urine 1 | 14 | 6.4 | 0.6 | 9.1 |
| urine 2 | 14 | 19.8 | 1.2 | 6.2 |
| urine 3 | 14 | 35.2 | 2.3 | 6.6 |

[a]Fourteen separate assays on 14 days (duplicate of each sample)

(c) Dilution curve

Figure 7:
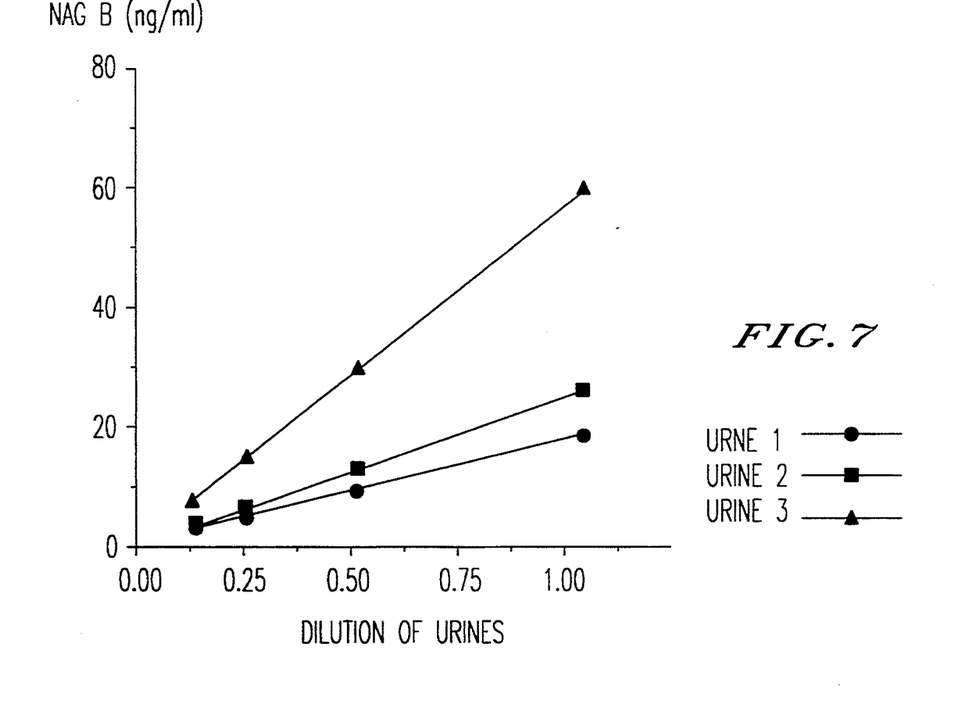
FIG. 7 Dilution curves of three urinary samples having different concentrations of NAG isozyme B.

The dilution curves of three urinary samples having different concentration are shown in FIG. 7. They possess excellent linearity.

(d) Analytical recovery of the standard added to urine

The recovery of standard antigen added to three urinary samples having different concentration ranged from 91% to 114% as shown below in Table 3.

TABLE 3

Analytical Recovery of Standard Added to Urines

| Urine No. | Endogenous NAG isozyme B ng/ml | Added ng/ml | Found[a] ng/ml | Recovery % |
|---|---|---|---|---|
| 1 | 8.9 | 5.0 | 5.5 | 110 |
|   | 8.9 | 12.5 | 12.9 | 103 |
|   | 8.9 | 25.0 | 23.9 | 96 |
| 2 | 13.1 | 12.5 | 11.4 | 91 |
|   | 13.1 | 25.0 | 25.4 | 102 |
|   | 13.1 | 50.0 | 47.9 | 96 |
| 3 | 27.3 | 12.5 | 14.2 | 114 |
|   | 27.3 | 25.0 | 28.1 | 112 |
|   | 27.3 | 50.0 | 46.1 | 92 |

Increase in NAG isozyme B over endogenous NAG isozyme B (e) Measurement of NAG isozyme B in the urine of a normal healthy human NAG isozyme B in urine of normal healthy human as measured by age and sex: The means at early morning (n=137, Table 4) and the other time (n=177, Table 5) were 4.2 μg and 3.3 μg per 1 g of creatinine, respectively.

TABLE 4

| Age | Sex | Number of individuals | NAG-B activity ng/ml | NAG-B activity μg/g Cr. |
|---|---|---|---|---|
| 20-29 | male | 3 | 5.6 ± 2.6 | 1.9 ± 0.9 |
|   | female | 4 | 8.6 ± 6.0 | 3.8 ± 2.0 |
| 30-39 | male | 20 | 4.2 ± 3.5 | 3.2 ± 4.2 |
|   | female | 6 | 6.0 ± 1.4 | 4.3 ± 1.0 |
| 40-49 | male | 20 | 7.7 ± 6.1 | 4.6 ± 3.5 |
|   | female | 11 | 4.9 ± 2.5 | 6.3 ± 3.9 |
| 50-59 | male | 20 | 5.4 ± 5.5 | 4.1 ± 3.1 |
|   | female | 20 | 4.7 ± 2.1 | 3.8 ± 2.7 |
| 60-69 | male | 13 | 6.6 ± 3.9 | 6.1 ± 5.0 |
|   | female | 20 | 3.9 ± 1.8 | 3.4 ± 1.5 |
|   | male | 76 | 5.9 ± 5.0 | 4.2 ± 3.9 |
|   | female | 61 | 4.1 ± 2.9 | 4.2 ± 2.7 |
| total |   | 137 | 5.1 ± 4.3 | 4.2 ± 3.4 |

TABLE 5

| Age | Sex | Number of individuals | NAG-B activity ng/ml | NAG-B activity μg/g Cr. |
|---|---|---|---|---|
| 20-29 | male | 20 | 3.2 ± 2.4 | 1.9 ± 0.9 |
|   | female | 16 | 4.3 ± 3.6 | 3.2 ± 1.3 |
| 30-39 | male | 20 | 3.3 ± 1.9 | 2.1 ± 1.0 |
|   | female | 19 | 2.8 ± 2.2 | 2.7 ± 1.8 |
| 40-49 | male | 21 | 2.5 ± 1.6 | 2.6 ± 1.6 |
|   | female | 20 | 3.2 ± 2.8 | 3.3 ± 2.5 |
| 50-59 | male | 19 | 3.8 ± 3.0 | 4.2 ± 1.7 |
|   | female | 20 | 2.8 ± 2.3 | 4.1 ± 2.1 |
| 60-69 | male | 9 | 4.6 ± 4.0 | 5.8 ± 3.5 |
|   | female | 13 | 3.3 ± 2.0 | 4.7 ± 2.0 |
|   | male | 89 | 3.3 ± 2.5 | 3.0 ± 2.1 |
|   | female | 88 | 3.2 ± 2.6 | 3.5 ± 2.1 |
| total |   | 177 | 3.3 ± 2.6 | 3.3 ± 2.1 |

From these results, it may be concluded that the present sandwich EIA makes it possible to detect NAG isozyme B quantitatively and reproducibly. This sandwich EIA needs less amount of sample (25 μl), is simpler, and makes it possible to treat a larger number of samples than the conventional NAG isozyme analysis which utilizes chromatography or electrophoresis. Furthermore, in this sandwich EIA, an edge effect, a defect of an assay using a plate, has not been observed. In view of these results the sandwich EIA of this invention should be adaptable for routine clinical work.

Having now fully described the invention, it will be apparent to one of ordinary skill in the art that many changes and modifications can be made thereto without departing from the spirit or scope of the invention as set forth herein.

What is claimed as new and desired to be secured by Letters Patent of United States is:

1. A monoclonal antibody selected from the group consisting of monoclonal antibody Hex 31 produced by Hybridoma Hex 31 (FERM BP-3858) and monoclonal antibody Hex 32 produced by Hybridoma Hex 32 (FERM BP-3859), wherein said monoclonal antibody recognizes β-N-acetylglucosaminidase (NAG) isozyme B with greater specificity than NAG isozyme A.

2. A sandwich immunoassay for detecting the presence of NAG isozyme B, comprising:

(1) contacting a sample with an immobilized monoclonal antibody and a labelled monoclonal antibody such that NAG isozyme B present in said sample forms an immobilized antibody-NAG isozyme B-labelled antibody complex, wherein said immobilized monoclonal antibody is contacted with said sample at pH 4.5-5.2 and wherein said immobilized monoclonal antibody is monoclonal antibody Hex 31 produced by Hybridoma Hex 31 (FERM BP-3858) and wherein said labelled monoclonal antibody is monoclonal antibody Hex 32 produced by Hybridoma Hex 32 (FERM BP-3859); and (2) detecting the amount of said immobilized antibody-NAG isozyme B-labelled antibody complex.

3. A sandwich immunoassay for detecting the presence of NAG isozyme B, which comprises the steps of:

(1) contacting an immobilized monoclonal antibody and a labelled monoclonal antibody with a sample such that NAG isozyme B present in said sample forms a sandwich complex of immobilized antibody-NAG isozyme B-labelled antibody, wherein said immobilized monoclonal antibody is contacted with said sample at pH 4.5-5.2 and wherein said immobilized monoclonal antibody is monoclonal antibody Hex 31 produced by Hybridoma Hex 31 (FERM BP-3858) and wherein said labelled monoclonal antibody is monoclonal antibody Hex 32 produced by Hybridoma Hex 32 (FERM BP-3859); and (2) detecting either the complexed or uncomplexed labelled monoclonal antibody.

4. The sandwich immunoassay according to claim 3, which further comprises the steps of:

(1) immobilizing said monoclonal antibody on a carrier to give said immobilized monoclonal antibody; and (2) labeling said monoclonal antibody to give said labelled monoclonal antibody.

5. The sandwich immunoassay according to claim 3, wherein the step of contacting said immobilized monoclonal antibody and said labelled monoclonal antibody with said sample is simultaneously or sequentially carried out.

6. The sandwich immunoassay according to claim 3, wherein in step (1) said sample is contacted with said immobilized monoclonal antibody such that NAG isozyme B present in said sample forms an immobilized antibody-NAG isozyme B complex and thereafter, said immobilized antibody-NAG isozyme B complex is contacted with said labelled monoclonal antibody such that said immobilized antibody-NAG isozyme B-labelled antibody complex is formed.

7. The sandwich immunoassay according to claim 6, wherein the contacting with said immobilized monoclonal antibody is effected at a pH of from 4.5–5.2 and the contacting with said labeled monoclonal antibody is effected at a pH of from 7–7.4.

8. The sandwich immunoassay according to claim 3, wherein in step (1) said sample is contacted with said labelled monoclonal antibody such that NAG isozyme B present in said sample forms a labelled antibody-NAG isozyme B complex and thereafter, said labelled antibody-NAG isozyme B complex is contacted with said immobilized monoclonal antibody such that said immobilized antibody-NAG isozyme B-labelled antibody complex is formed.

9. The sandwich immunoassay according to claim 8, wherein the contacting with said immobilized monoclonal antibody is effected at a pH of from 4.5–5.2 and the contacting with said labeled monoclonal antibody is effected at a pH of from 7–7.4.

10. A kit for assaying the presence of NAG isozyme B, which comprises an immobilized monoclonal antibody Hex 31 produced by Hybridoma Hex 31 (FERM BP-3858) and a labelled monoclonal antibody Hex 32 produced by Hybridoma Hex 32 (FERM BP-3859) according to claim 1, wherein when a sample is contacted with said kit NAG isozyme B present in said sample is sandwiched between said immobilized monoclonal antibody and said labelled monoclonal antibody.

11. The kit according to claim 10, further comprising a buffer with a pH of from 4.5–5.2.

* * * * *